United States Patent
Stark et al.

[11] Patent Number: 6,066,339
[45] Date of Patent: May 23, 2000

[54] ORAL MORPHINE MULTIPARTICULATE FORMULATION

[75] Inventors: Paul Stark; Sean Cunningham; Jagathesan Moodley, all of Althone, Ireland

[73] Assignee: Elan Corporation, plc, Dublin, Ireland

[21] Appl. No.: 08/977,965

[22] Filed: Nov. 25, 1997

Related U.S. Application Data

[60] Provisional application No. 60/062,525, Oct. 17, 1997.

[51] Int. Cl.⁷ .................................................. A61K 9/14
[52] U.S. Cl. ........................... 424/489; 424/464; 424/468; 424/469; 424/471; 424/472; 424/482; 424/484; 424/487
[58] Field of Search ..................... 424/464, 468, 424/469, 471, 472, 482, 484, 487, 489

[56] References Cited

U.S. PATENT DOCUMENTS

| | | | |
|---|---|---|---|
| 4,609,542 | 9/1986 | Panoz et al. | 424/19 |
| 4,610,875 | 9/1986 | Panoz et al. | 424/80 |
| 4,663,150 | 5/1987 | Panoz et al. | 424/494 |
| 4,716,040 | 12/1987 | Panoz et al. | 424/459 |
| 4,721,619 | 1/1988 | Panoz et al. | 424/459 |
| 4,726,951 | 2/1988 | Panoz et al. | 424/465 |
| 4,769,236 | 9/1988 | Panoz et al. | 424/80 |
| 4,820,521 | 4/1989 | Panoz et al. | 424/458 |
| 4,826,688 | 5/1989 | Panoz et al. | 424/473 |
| 4,863,742 | 9/1989 | Panoz et al. | 424/473 |
| 4,891,230 | 1/1990 | Geoghegan et al. | 424/461 |
| 4,894,240 | 1/1990 | Geoghegan et al. | 424/497 |
| 4,898,737 | 2/1990 | Panoz et al. | 424/468 |
| 4,917,899 | 4/1990 | Geoghegan et al. | 424/461 |
| 4,970,075 | 11/1990 | Oshlack | 424/451 |
| 5,002,776 | 3/1991 | Geoghegan et al. | 424/497 |
| 5,178,868 | 1/1993 | Malmquist-Granlund et al. | 424/490 |
| 5,202,128 | 4/1993 | Morella et al. | 424/469 |
| 5,219,621 | 6/1993 | Geoghegan et al. | 424/462 |
| 5,229,131 | 7/1993 | Amidon et al. | 424/451 |
| 5,273,760 | 12/1993 | Oshlack et al. | 424/480 |
| 5,286,493 | 2/1994 | Oshlack et al. | 424/468 |
| 5,330,766 | 7/1994 | Morella et al. | 424/490 |
| 5,336,504 | 8/1994 | Geoghegan et al. | 424/462 |
| 5,364,620 | 11/1994 | Geoghegan et al. | 424/497 |
| 5,378,474 | 1/1995 | Morella et al. | 424/469 |
| 5,411,745 | 5/1995 | Oshlack et al. | 424/456 |
| 5,478,577 | 12/1995 | Sackler et al. | 424/489 |
| 5,520,931 | 5/1996 | Persson et al. | 424/473 |
| 5,593,694 | 1/1997 | Hayashida et al. | 424/468 |
| 5,593,695 | 1/1997 | Merrill et al. | 424/480 |
| 5,616,345 | 4/1997 | Geoghegan et al. | 424/497 |
| 5,656,291 | 8/1997 | Olsson et al. | 424/458 |
| 5,667,805 | 9/1997 | Merrill et al. | 424/473 |
| 5,741,524 | 4/1998 | Staniforth et al. | 424/489 |

FOREIGN PATENT DOCUMENTS

| | | |
|---|---|---|
| 0 365 947 | 5/1990 | European Pat. Off. . |
| 0 377 518 | 7/1990 | European Pat. Off. . |
| 0 609 961 | 8/1994 | European Pat. Off. . |
| 0 631 781 | 1/1995 | European Pat. Off. . |
| 0 636 370 | 1/1995 | European Pat. Off. . |
| 0 647 448 | 4/1995 | European Pat. Off. . |
| WO 94/03161 | 2/1994 | WIPO . |
| WO 94/22431 | 10/1994 | WIPO . |
| WO 95/14460 | 1/1995 | WIPO . |

*Primary Examiner*—Thurman K. Page
*Assistant Examiner*—Lakshmi Channavajjala
*Attorney, Agent, or Firm*—Marla J. Church

[57] ABSTRACT

An oral morphine multiparticulate formulation for once-daily administration to a patient, comprising sustained release particles each having a core containing water soluble morphine and an osmotic agent, the core being coated with a rate-controlling polymer coat comprised of ammonio methacrylate copolymers in an amount sufficient to achieve therapeutically effective plasma levels of morphine over at least 24 hours in the patient.

27 Claims, 4 Drawing Sheets

ORAL MORPHINE MULTIPARTICULATE FORMULATION

This application claims the benefit of U.S. Provisional Application No. 60/062,525, filed Oct. 17, 1997.

FIELD OF THE INVENTION

This invention relates to an oral morphine formulation which is suitable for once-daily administration and which minimises the risk of side effects caused by morphine attributable to fluctuations in plasma morphine levels.

BACKGROUND OF THE INVENTION

Morphine is typically used in therapy in the form of morphine sulfate or a hydrate thereof.

Morphine sulfate is an opioid compound with specific affinity for the receptors $\mu$, $\delta$ and $\kappa$. The principal actions of therapeutic value are analgesia and sedation. The precise mechanism of the analgesic action is unknown. Specific opioid receptors have been located in the brain and the spinal cord and are likely to play a role in the expression of analgesic effects.

Following oral administration of a given dose of morphine, the amount eventually absorbed is essentially the same irrespective of the formulation. Morphine is subject to presystemic elimination (metabolism in the gut wall and liver) and therefore only 40% of the administered dose reaches systemic circulation. Virtually all morphine is converted to glucuronide metabolites; morphine-3-glucuronide (present in highest concentrations but inactive) and morphine-6-glucuronide. A large body of evidence from animal experiments show that morphine-6-glucuronide is a potent $\mu$-opioid agonist, with the potential to contribute to morphine's analgesic response.

Morphine undergoes significant hepatic first pass metabolism to form morphine-6-glucuronide. About 90% of a dose of morphine is excreted in the urine mainly as either this conjugate or as morphine-3-glucuronide, while the remainder is excreted in the bile.

Morphine sulphate is generally indicated for the relief of moderate to severe pain most particularly in palliative care, surgery and myocardial infarction. It is intended for use in patients who require repeated dosing with potent opioid analgesic over periods of more than a few days.

Various slow/sustained release morphine formulations have been developed and are described in the literature.

Extended release oral morphine sulphate preparations are considered to be clinically significant as they impart equivalent to superior analgesia with respect to immediate release forms in addition to reducing the likelihood of morphine associated side effects. Morphine sulphate is currently available as a bd dosage form as MS Contin™ Tablets (Napp) available as 10 mg, 30 mg, 60 mg, 100 mg and 200 mg active per unit dose. Pain specialists have indicated the requirement for a once daily extended release preparation to avoid break-through pain. Once daily morphine products currently available are those sold under the Trade Marks MST Continus Long and Kapanol.

Apart from achieving sustained release of morphine over extended periods of time, for true therapeutic efficacy a sustained release morphine formulation should achieve therapeutically effective plasma levels of morphine over at least 24 hours coupled with minimum fluctuations in plasma morphine levels.

Morphine-related side effects are a feature of morphine therapy. These side effects include nausea and vomiting, constipation, sedation, confusion and loss of appetite. It has been suggested that the use of modified release morphine formulations, apart from their convenience and their ability to provide continuous analgesia, may also result in a lower incidence and severity of morphine-related side effects (Gourlay, G. K. et al., Pain (1997) 69, 295–302.

U.S. Pat. No. 5,478,577, describes and claims a method for providing effective pain management in humans for a time period of about 24 hours using an opioid analgesic such as morphine in a solid, controlled-release oral dosage form. This dosage form following administration provides a rapid rate of initial rise of the plasma concentration of the opioid, such that peak plasma levels thereof occur from about 2 to about 8 hours and which provides large peak to trough fluctuations in opioid levels even after repeated dosing. Such large peak to trough fluctuations would be expected to maximise attendant morphine-related side effects.

In order to minimise morphine-related side effects, which are a distinct disadvantage and which add to the suffering of those experiencing long-term pain such as cancer patients, what is required is a formulation which exhibits minimal peak to trough fluctuations, namely a substantially flat plasma profile over the dosage period.

A further requirement of a therapeutically effective morphine sustained release formulation is one which maintains a high plasma concentration of morphine over the dosage period.

In case of U.S. Pat. No. 5,478,577 mentioned above peak plasma levels occur from about 2 to about 8 hours after administration.

EP 631,781 discloses morphine formulations having extended controlled release with peak plasma levels in vitro occurring from about 2 to about 6 hours after administration.

Likewise, EP 636,370 discloses morphine-containing sustained release formulations which are described as giving in vivo peak plasma levels relatively early after administration, that is from 1.0 to 6 hours after administration and a $W_{50}$ (a parameter defined therein as the width of the plasma profile at 50% $C_{MAX}$ i.e. the duration over which the plasma concentrations are equal to or greater than 50% of the peak concentration) for morphine of between 4 and 12 hours.

EP 609,961 discloses sustained released compositions which can contain morphine as active ingredient and which can maintain an active ingredient blood level at steady state of at least 75% of maximum blood level (t ⊕0.75 $C_{max}$) for approximately 3.5 hours or greater and so that the time at which the active ingredient reaches its maximum concentration ($t_{max}$) is 4.5 hours or greater.

WO 94/22431 discloses an oral morphine preparation which achieves a mean serum concentration of morphine of at least 50% of the maximum serum concentration during at least 12 hours after administration of a single dose of the preparation.

SUMMARY OF THE INVENTION

The invention provides an oral morphine multiparticulate formulation for once-daily administration to a patient, comprising sustained release particles each having a core containing water soluble morphine and an osmotic agent, the core being coated with a rate-controlling polymer coat comprised of ammonia methacrylate copolymers in an amount sufficient to achieve therapeutically effective plasma levels of morphine over at least 24 hours in the patient.

As demonstrated hereinbelow, the formulation according to the invention achieves therapeutically effective plasma levels of morphine over at least 24 hours coupled with a substantially flat plasma profile. Thus, the formulation according to the invention, which exhibits minimal fluctuations in plasma levels of morphine over the dosage period, should serve to minimise the occurrence of morphine-related side effects and thus ensure more efficacious morphine therapy than sustained release formulations currently available and/or as described in the prior art set out above.

Additionally, because of the substantially flat morphine plasma bioprofile, titrating the formulation according to this invention to a particular patient's need is safer and easier than the formulations set out in the prior art above.

The formulations according to the invention are also bioequivalent under single dosage and steady state conditions to instant release oral solution (Q4h×6), twice daily and other once-daily formulations. This bioequivalence combined with the substantially flat plasma bioprofile for the formulations according to this invention allows the formulations to be effective in preventing break-through pain.

According to one embodiment a portion or all of the sustained release particles further comprise an immediate release coating applied onto the rate-controlling polymer coat, which immediate release coating comprises water soluble morphine and optionally an osmotic agent.

Although frequently in on-going pain management therapy a patient will already by taking morphine as part of his/her medication when prescribed a formulation in accordance with the invention, there will be occasions when an immediate release of morphine is required by such patients. However, the formulation according to the invention will also be suitable for use in managing pain in other situations, such as in post-operative pain, where it is also important to control morphine-related side effects. Thus, the formulation according to the invention may be characterized by both a flat plasma profile and a rapid onset of action. Such a rapid onset of action is achieved by including an immediate release morphine component in the formulation.

In an alternative embodiment, the formulation can contain a portion of immediate release particles each comprising a core of water soluble morphine and optionally an osmotic agent.

The immediate release particles can comprise immediate release pellets or granulates.

The formulation according to the invention may also comprise at least two populations of sustained release particles having different in vitro dissolution profiles.

Preferably, the formulation releases morphine in vivo) following single dose administration such that the duration over which the plasma level of morphine is equal to or greater than 50% of the peak plasma concentration is 20 hours or greater, more preferably 24 hours or greater, especially 30 hours or greater.

Also, preferably the formulation releases morphine in vivo following single dose administration such that the duration over which the plasma level of morphine is equal to or greater than 75% of the peak plasma concentration is 6 hours or greater, more preferably 12 hours or greater, most preferably 18 hours or greater.

Further, preferably the formulation releases morphine in vivo at steady state such that the plasma level of morphine over the entire 24 hour dosing period is equal to or greater than 50% of the peak plasma concentration.

Still further, preferably the formulation releases morphine in vivo at steady state such that the duration over which the plasma level of morphine over the 24 hour dosing period is equal to or greater than 75% of the peak plasma concentration is 12 hours or greater.

Also preferably, the formulation according to the invention provides a dissolution profile in aqueous media such that about 3 to 25% of the water soluble morphine is released after 1 hour; about 5 to 35% is released after 4 hours; about 25 to 65% is released after 9 hours; about 35 to 75% is released after 12 hours and at least 70% is released after 24 hours.

In an alternative embodiment the formulation provides a dissolution profile in aqueous media such that about 10 to 15% of the water soluble morphine is released after 1 hour; about 15 to 30% is released after 4 hours; about 35 to 50% is released after 9 hours; about 45 to 65% is released after 12 hours and at least 80% is released after 24 hours.

Also, in a preferred embodiment greater than 80% of the formulation is comprised of sustained release particles.

In a preferred embodiment the rate-controlling polymer coat contains Ammonia Methacrylate Copolymer Type A and Ammonia Methacrylate Copolymer Type B as described in USP/NF in a ratio of 15:85 to 1:99, more especially about 5:95.

Such copolymers are manufactured and marketed by Rohm, GmbH, Darmstadt, Germany.

Most preferably, the rate-controlling polymer coat contains a 5:95 mixture of Eudragit RL:Eudragit RS most especially Eudragit RL 12.5:Eudragit RS 12.5.

The osmotic agent according to the invention refers to a pharmaceutically acceptable material that enhances the passage of the water soluble morphine through the rate-controlling polymer coat or through the tissue in the gastrointestinal tract (GIT). Without being limited to any particular theoretical mechanism, the osmotic agent may enhance the absorption of water soluble morphine by creating a local pH and/or chemical potential environment.

Preferably, the osmotic agent is an organic acid, a pharmaceutically acceptable salt, a GIT absorption enhancer or a combination thereof. Suitable osmotic agents include but are not limited to adipic acid, ascorbic acid, citric acid, malic acid, succinic acid, tartaric acid, lactic acid, monopotassium citrate, potassium acid tartrate, sodium fumarate, sodium dihydrogen phosphate, sodium bisulfate, sodium metabisulfate or combinations thereof.

Further, preferably, the osmotic agent is an organic acid selected from fumaric acid, adipic acid, ascorbic acid, citric acid, tartaric acid, lactic acid, malic acid and succinic acid, more especially fumaric acid.

Preferably, the water soluble morphine and osmotic agent are present in the cores in a ratio of 2.5:1 to 1:2.5, more especially about 1:1.

Preferably, the water soluble morphine is morphine sulfate or a hydrate thereof, especially the pentahydrate.

Morphine sulphate pentahydrate typically contains ~9–12% bound water. A portion of this water is typically dried off during routine processing. However, loss of water of hydration can affect the dissolution profile and thus the efficacy of the formulation. Thus, we have found that it is beneficial to prevent the loss of water of hydration during the drying process involved in manufacturing the multiparticulate formulation according to the invention when morphine sulphate pentahydrate is used.

It has been found that about 3–4% by weight moisture content is beneficial on the basis of the moisture level of morphine sulphate in the formulation. However, as other excipients in the formulation may absorb moisture, a range of about 3–6% by weight moisture content for the formulation may be required. Preferably the cores for the sustained release particles are equilibrated at ambient conditions or dried at humidified conditions such as about 40–50° C. and about 30–60% relative humidity for 10–20 hours prior to being coated with the rate-controlling polymer coat so as to obtain a moisture content of about 3–6% by weight.

Still further preferably, the sustained release particles following application of the rate-controlling polymer coat are dried at a temperature of about 40–50° C. and about 30–60% relative humidity or are equilibrated at ambient conditions.

Preferably, the formulation contains between 10 mg and 200 mg of morphine sulfate or the equivalent amount of water soluble morphine.

In a preferred embodiment, the formulation is encapsulated, for example in hard or soft gelatin capsules.

The core, herein referred to as applied beads or IR beads, can be formed by building up the morphine active agent, osmotic agent, and, if desired, any pharmaceutically acceptable excipient(s) such as binders, surfactants and lubricants on an inert core. The inert core is preferably a non-pareil seed of sugar/starch having an average diameter in the range 0.2–1.4 mm, more especially, 0.3–0.8 mm, most especially 0.5–0.6 mm.

The morphine active agent, the osmotic agent and, if desired, pharmaceutically acceptable excipient(s) are blended to form a homogeneous powder herein referred to as the active blend. This blend can then be applied to the inert core using an application solution.

The blend is optionally passed through an appropriate mesh screen using a milling machine. In the case of coating in a conventional coating pan, alternate layers of the application solution and the powder are applied to the central inert core to build up the multi-layer arrangement of the core. In the case of an automatic coating system, the application solution and the powder are applied, simultaneously, in conventional manner. Conventional automated coating systems include for example a CF granulator or other suitable fluidized bed based systems.

The application solution comprises one or more binder(s) dissolved/suspended in a suitable solvent or mixture of solvents. Suitable binding agents include polyvinylpyrrolidone, starch and gelatin. A preferred binder is polyvinylpyrrolidone. Preferably, between 5 and 50 parts of the central inert cores are used relative to the homogeneous powder.

The completed cores preferably have an average diameter in the range 0.4–1.8 mm, more especially in the range 0.7–1.5 mm.

The pharmaceutically acceptable excipients can be homogeneously mixed with the water soluble morphine to form the active blend. These materials may include ingredients known to act as lubricants and surfactants. Representative excipients include: microcrystalline cellulose (such as that sold under the Trade Mark AVICEL); colloidal silicon dioxide (such as that sold under the Trade Mark AEROSIL); lactose; talc; starch; sorbitol; sodium lauryl sulphate; and cyclodextrin. These may be used singly or in combination with each other. Especially preferred excipients are talc and sodium lauryl sulphate.

The sustained release particles are formed by coating the applied beads with a rate-controlling polymer coat comprised of ammonio methacrylate copolymers such as those sold under the Trade Mark EUDRAGIT.

EUDRAGIT polymers are polymeric lacquer substances based on acrylates and/or methacrylates. The polymeric materials sold under the Trade Mark EUDRAGIT RL and EUDRAGIT RS are acrylic resins comprising copolymers of acrylic and methacrylic acid esters with a low content of quaternary ammonium groups and are described in the "EUDRAGIT" brochure of Messrs. Rohm Pharma GmbH (1984) wherein detailed physical-chemical data of these products is given. The ammonium groups are present as salts and give rise to the permeability of the lacquer films. EUDRAGIT RL and RS are freely permeable (RL) or slightly permeable (RS), respectively, independent of pH.

The rate-controlling polymer coat may be built up by applying a plurality of coats of polymer solution or suspension to the core as hereinafter described. The polymer solution or suspension contains the polymer(s) dissolved or suspended, respectively, in a suitable aqueous or organic solvent or mixture of solvents, optionally in the presence of a lubricant. Suitable lubricants are talc, stearic acid, magnesium stearate and sodium stearate. A particularly preferred lubricant is talc.

The polymer solution or suspension may optionally include a plasticizing agent. Suitable plasticizing agents include polyethylene glycol, propylene glycol, glycerol, triacetin, dimethyl phthalate, diethyl phthalate, dibutyl phthalate, dibutyl sebacate, triethyl citrate, tributyl citrate, triethyl acetyl citrate, castor oil and varying percentages of acetylated monoglycerides.

Suitable organic solvents include isopropyl alcohol or acetone or a mixture thereof.

The polymer solution or suspension may be applied to the active cores in a conventional coating pan as indicated or, alternatively, and preferably using an automated system such as a CF granulator, for example, a FREUND CF granulator, a GLATT fluidised bed processor, an AEROMATIC, a modified ACCELA-COTA or any other suitably automated bead coating equipment (FREUND, GLATT, AEROMATIC and ACCELA-COTA are all Trade Marks).

Preferably 2–75 ml of polymer solution/suspension is applied per application per kilogram of cores. In an automated system the total amount of polymer solution/ suspension applied to the cores is similar to that applied in a conventional coating pan, except that the polymer solution/suspension may be applied continuously. Preferably, when a coating pan is used the rate-controlling polymer coat is applied to a given target polymer coating weight.

The method of manufacturing the oral morphine multiparticulate formulation in accordance with the invention is based upon coating drug loaded cores with rate controlling polymers to achieve a target dissolution rate. Drug release from these beads is diffusion controlled as the polymer swells and becomes permeable, thus, allowing for controlled release in the GIT. To achieve an appropriate dissolution profile, in addition to accommodating an efficient manufacturing process, the following critical parameters require consideration (a) drug solubility
(b) drug and excipient particle size
(c) drug: osmotic agent ratio
(d) drug: coated bead surface area ratio
(e) bead size
(f) coating polymer
(g) applied bead binding polymer
(h) processing conditions as will be apparent from the following Examples.

Figure 1:
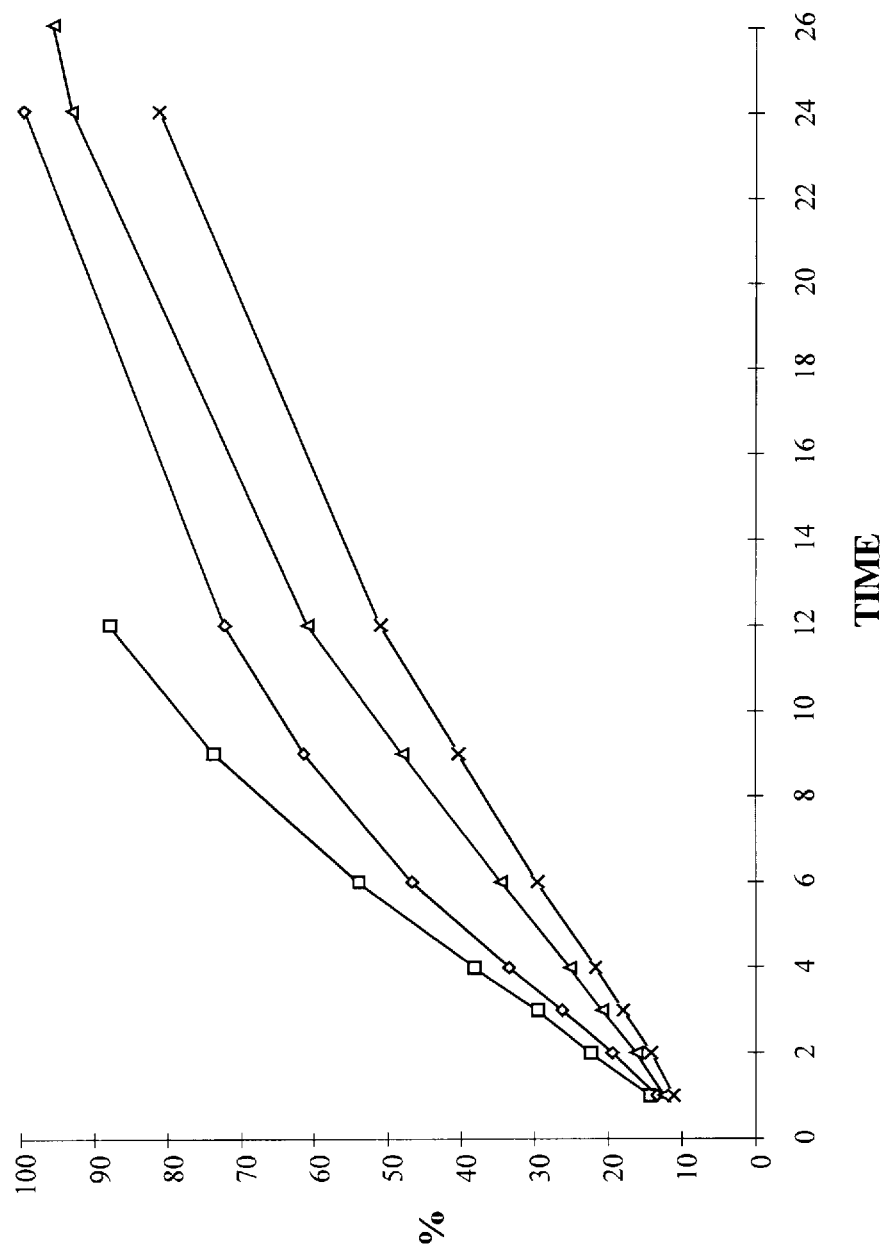
FIG. 1 shows dissolution (%) vs time (h.) for the formulations of Examples 1–3 and the reference product of Example 7 in aqueous media.
Figure 2:
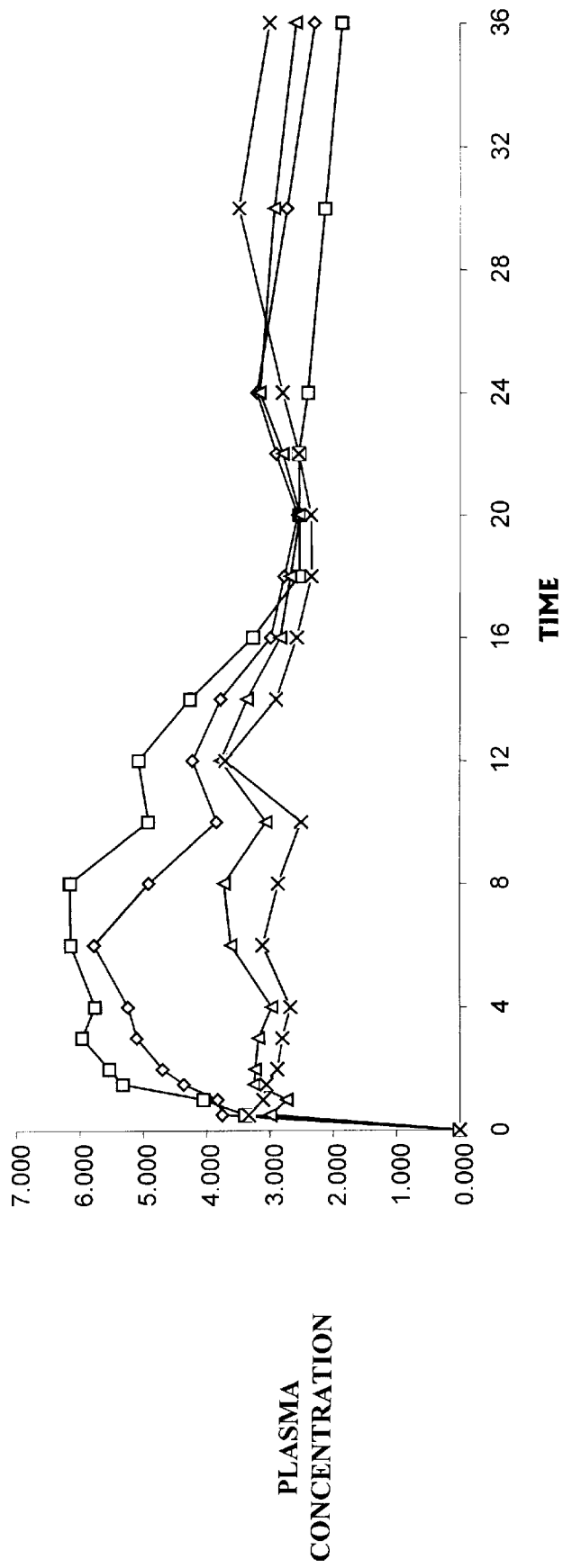
Figure 3:
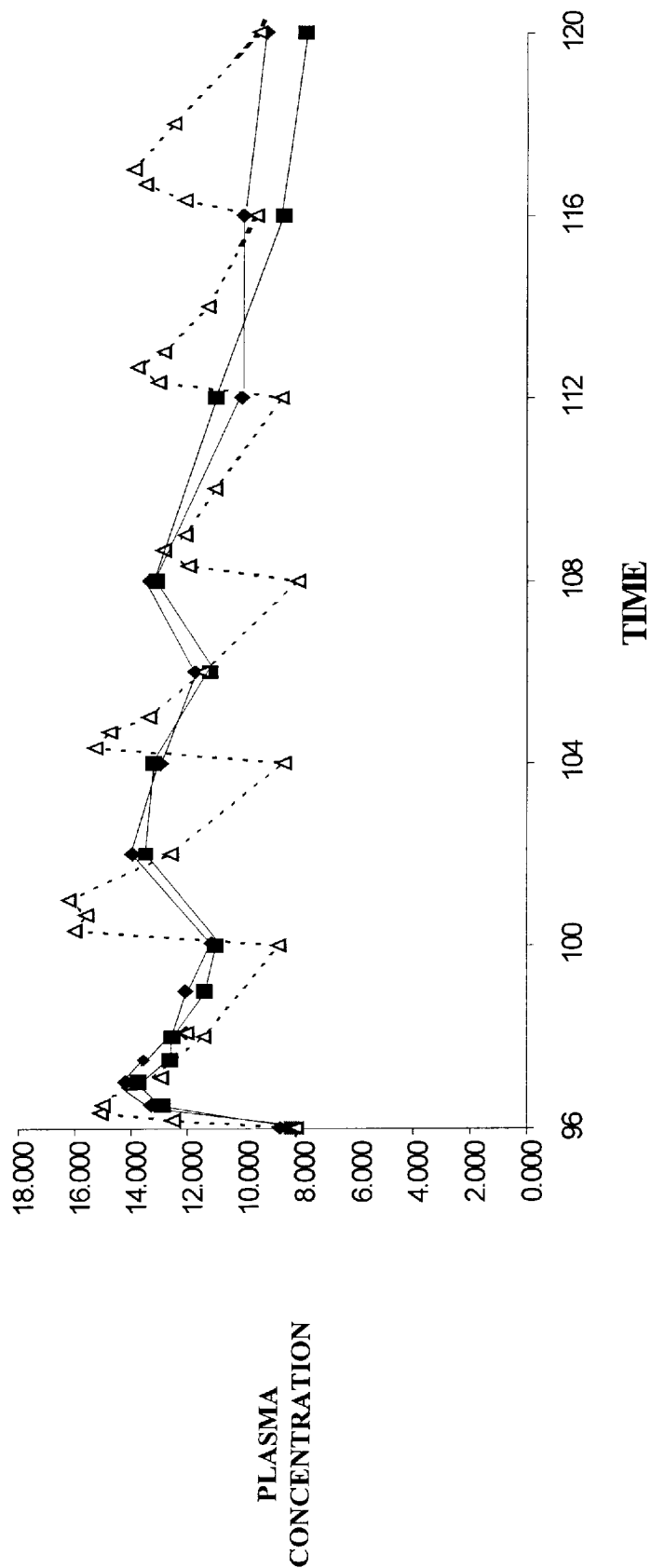

Curve —☐— corresponds to the reference product of Example 7, curve —◇— corresponds to the product of Example 3, curve —△— corresponds to the product of Example 1 and curve —x— corresponds to the product of Example 2;

FIG. 2 shows mean morphine plasma concentration (ng/ml) vs time (h.) for the products described under FIG. 1 following single dose administration. Curves —☐—, —◇—, —△— and —x— correspond to the same products as the corresponding curves of FIG. 1;

FIG. 3 shows mean plasma morphine concentration (ng/ml) vs time (h.) for the formulations of Examples 1 and 2 relative to the reference as described in Example 9 at steady state.

Figure 4:
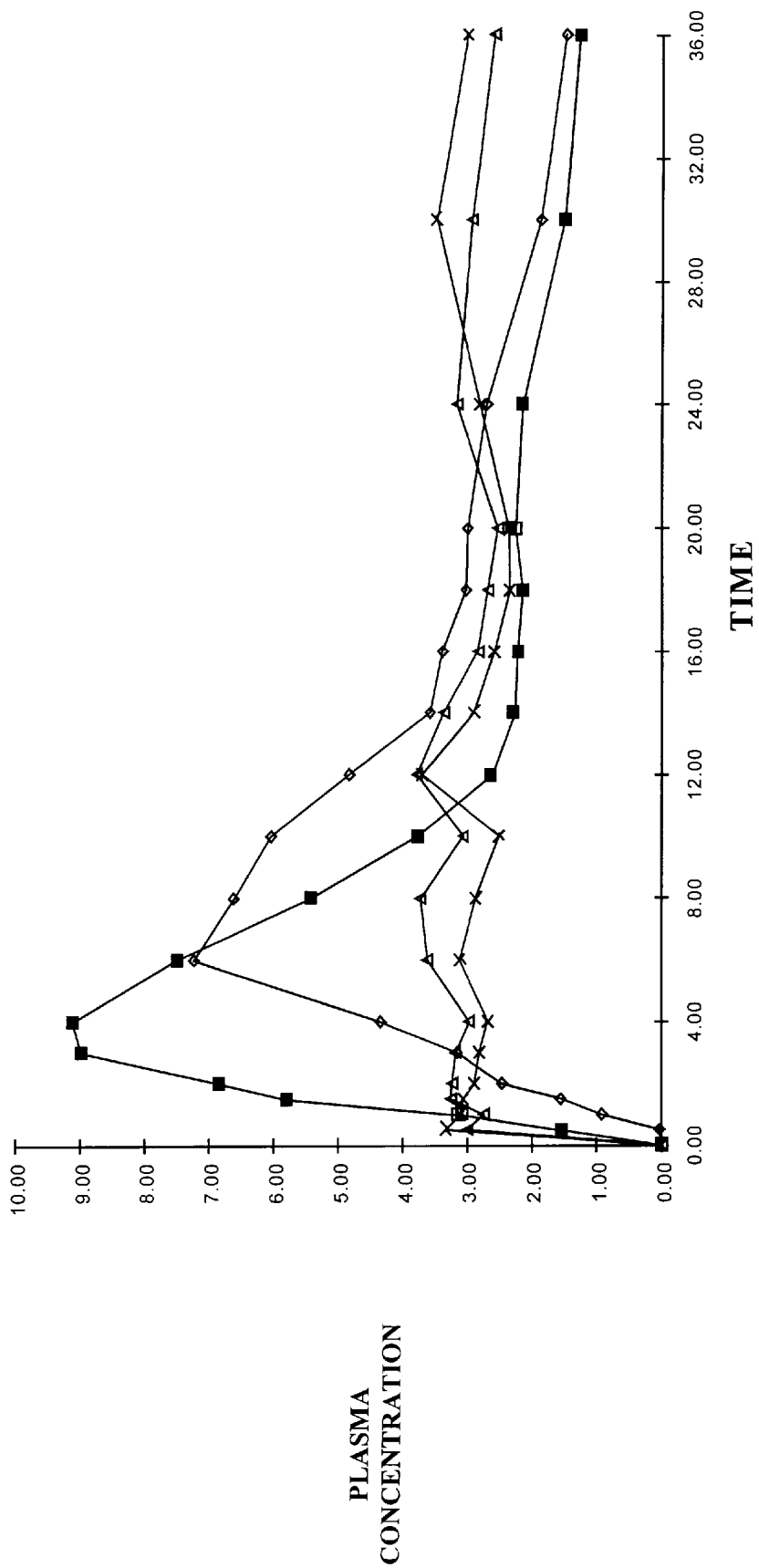

Curve —■— corresponds to the product of Example 1, curve —◆— corresponds to the product of Example 2, and curve —▲— corresponds to the reference product of Example 9; and FIG. 4 shows morphine plasma concentrations (single dose) (ng/ml) vs time (h.) for the products of Examples 1 and 2 relative to the reference products 1 and 2 of Example 11.

Curve —◇— corresponds to reference product: 1, curve —■— corresponds to reference product 2, curve —△— corresponds to the product of Example 1 and curve —x— corresponds to the product of Example 2.

DETAILED DESCRIPTION OF THE INVENTION

EXAMPLE 1

Morphine Sulphate 60 mg Capsules

Morphine sulphate capsules containing a blend of SR beads and IR beads and having the following composition:

| INGREDIENT | mg/cap. | mg/g |
|---|---|---|
| ACTIVE | | |
| Morphine sulphate | 60 | 310.0 |
| EXCIPIENTS | | |
| Sugar spheres | 30 | 155.0 |
| Fumaric acid | 60 | 310.0 |
| Talc | 29.1 | 150.3 |
| Sodium lauryl sulphate | 0.30 | 1.5 |
| Povidone (Kollidon 30) | 9.8 | 50.6 |
| Ammonio Methacrylate Copolymer Type A (Eudragit RL) | 0.22 | 1.1 |
| Ammonio Methacrylate Copolymer Type B (Eudragit RS) | 4.15 | 21.4 |
| Isopropyl alcohol* | — | — |
| Acetone* | — | — |

*Used in processing, occurring in trace amounts in finished product.

were manufactured as follows:

Applied Beads (IR beads)

Morphine sulphate (49.38% w/w), fumaric acid (49.38% w/w) talc (0.988% w/w) and sodium lauryl sulphate (0.25%) (collectively the active blend) were blended in a tumble blender and comminuted. The blend was applied in a suitable fluidized bed system onto non pareil seeds using a suitable binder, such as Povidone, from a suitable organic or aqueous solution, such as isopropyl alcohol. The resultant immediate release beads were dried for 20 h at 55° C. to obtain a moisture content of between 3–6%. The dried beads were then screened and appropriate fractions retained for further processing.

The applied beads were formed from:

Active blend 75.3%

Povidone solution (Solids) 6.1%

Non pareil seeds 18.6%

Sustained Release Beads (SR beads)

Prior to coating, the applied beads (immediate release) from above were exposed on drying trays at ambient conditions to allow equilibration of applied bead moisture content.

To coat the applied beads (IR), a coating solution comprising a 6.25% solution of Eudragit RS (95% w/w) and Eudragit RL (5% w/w) dissolved in isopropyl alcohol/acetone was sprayed onto a fluidised bed of applied beads. Talc was also added simultaneously via an auger feeder to prevent agglomeration. The resulting product consisted of a core (applied beads) coated with a rate-controlling polymer coat having 30.1 mg of polymer coat per gram of applied beads.

The coated beads were oven dried for 20 h. at 35° C. to remove residual solvent, then the coated beads were exposed at ambient conditions for 96 h. on drying trays to allow for moisture equilibration.

Thus, the materials used for the SR beads were applied beads: 81.8%; Eudragit RS/RL coating solution (solids): 2.5% and talc: 15.7%.

Encapsulation (90% SR beads/10% IR beads)

Morphine sulphate applied beads (10% w/w by potency) and the polymer coated beads (90% w/w by potency) from above were blended together using a tumble blender. The blended beads from above were filled into gelatin capsules to give a target strength of 60 mg per capsule.

EXAMPLE 2

Morphine Sulphate 60 mg Capsules

Morphine sulphate capsules containing a blend of two populations of SR beads and IR beads having the following composition:

| INGREDIENT | mg/cap. | mg/g |
|---|---|---|
| ACTIVE | | |
| Morphine sulphate | 60 | 309.6 |
| EXCIPIENTS | | |
| Sugar spheres | 30 | 154.8 |
| Fumaric acid | 60 | 309.6 |
| Talc | 29.1 | 150.2 |
| Sodium lauryl sulphate | 0.30 | 1.5 |
| Povidone (Kollidon 30) | 9.8 | 50.6 |
| Ammonio Methacrylate Copolymer Type A (Eudragit RL) | 0.22 | 1.1 |
| Ammonio Methacrylate Copolymer Type B (Eudragit RS) | 4.15 | 21.4 |
| Diethylphthalate | 0.22 | 1.1 |
| Isopropyl alcohol* | — | — |
| Acetone* | — | — |

*Used in processing, occurring in trace amounts in finished product were manufactured as follows:

Applied Beads (IR beads)

The applied beads were prepared in the same way as for the applied beads of Example 1.

Sustained Release Beads (SR beads)

Two SR components were prepared. SR component 1 was that used in Example 1 and was incorporated into the capsule at 45% by potency. The second SR component was prepared using a method that was comparable to that used for preparing the first SR component. However, the following differences apply.

1. The polymer coating solution contained 10% plasticiser (diethylphthalate)

Solution Formulation (solid basis)
   Eudragit RS 86.36%
   Eudragit RL 4.55%
   Diethylphthalate 9.09%; and 2. The coated beads were oven dried for 20 h. at 55° C. to remove residual solvent, then exposed at ambient conditions for 96 h. on drying trays to allow for moisture equilibration.

The second SR polymer coating was applied to the target weight of 30.1 mg polymer coat per gram of applied beads.

Thus, the materials used for second SR component beads were applied beads: 81.6%; plasticised Eudragit RS/RL coating solution solids: 2.7% and talc: 15.7%.

Encapsulation (45% 1st SR component; 45% 2nd SR component; and 10% IR)

Morphine sulphate applied beads (10% w/w by potency), 1st SR component beads (45% w/w by potency) and 2nd SR component beads (45% w/w by potency) were blended as given in Example 1 and filled into gelatin capsules to give a target strength of 60 mg per capsule.

EXAMPLE 3

Morphine Sulphate 60 mg Capsules

Morphine sulphate capsules comprising a blend of two populations of SR beads and IR beads having the following composition:

| INGREDIENT | mg/cap. | mg/g |
|---|---|---|
| ACTIVE | | |
| Morphine sulphate | 60 | 310.0 |
| EXCIPIENTS | | |
| Sugar spheres | 30 | 155.0 |
| Fumaric acid | 60 | 310.0 |
| Talc | 29.1 | 150.3 |
| Sodium lauryl sulphate | 0.30 | 1.5 |
| Povidone (Kollidon 30) | 9.8 | 50.6 |
| Ammonio Methacrylate Copolymer Type A (Eudragit RL) | 0.22 | 1.1 |
| Ammonio Methacrylate Copolymer Type B (Eudragit RS) | 4.15 | 21.4 |
| Isopropyl alcohol* | — | — |
| Acetone* | — | — |

*Used in processing occurring in trace amounts in finished product were prepared as follows:

Applied Beads (IR beads)

The applied beads were prepared in the same way as for those of Example 1.

Sustained Release Beads (SR beads)

Two sustained release components were prepared. SR Component 1 (65% of the formulation by potency) was the same as the SR beads used in Example 1. SR Component 2 (25% of the formulation by potency) was the same as SR beads used in Example 1 in terms of materials and quantities of materials used for manufacture. However, the following processing changes occurred.

1. The applied beads were dried for an additional 20 h. at 55° C. prior to coating; and
2. The SR Component 2 beads were dried at 55° C. for 20 h. post coating followed by 96 h. at ambient conditions.

Encapsulation (65% 1st SR Component; 25% 2nd SR Component; and 10% IR)

Morphine sulphate applied beads (10% w/w by potency), 1st SR component beads (65% w/w by potency) and 2nd SR component beads (25% w/w by potency) were blended as given in Example 1 and filled into gelatin capsules to give a target strength of 60 mg per capsule.

The mean dissolution data for the formulations of Examples 1–3 in aqueous medic is set out in Table 1 and is graphically represented in FIG. 1.

TABLE 1

MEAN DISSOLUTION RATES

| Time (h) | Example 1 medium | Example 2 slow | Example 3 fast |
|---|---|---|---|
| 1 | 12.4 | 11.1 | 13.4 |
| 2 | 16.2 | 14.2 | 19.4 |
| 3 | 20.8 | 17.9 | 26.2 |
| 4 | 25.2 | 21.7 | 33.4 |
| 6 | 34.5 | 29.6 | 46.6 |
| 9 | 48 | 40.3 | 61.4 |
| 12 | 60.9 | 50.9 | 72.2 |
| 24 | 93.2 | 81.3 | 99.7 |
| 26 | 95.7 | — | — |

EXAMPLE 4

Morphine Sulphate 60 mg Capsules

Morphine sulphate capsules were manufactured as follows:

Applied Beads (IR beads)

A mixture of morphine sulphate, fumaric acid, talc and sodium lauryl sulphate was applied to non pareil seeds in a CF Granulator using polyvinylpyrrolidone (PVP) in isopropyl alcohol solution as binder. These beads were then oven dried. The processing details for the manufacture of the applied beads are set forth in Table 2.

Sustained Release Beads (SR beads)

The applied beads from above were coated in a CF Granulator to 50%, 75% and 100% of the target weight for the polymer coat using a 95:5 mixture of Eudragit RS: Eudragit RL, 6.25% w/w solution in isopropyl alcohol as coating solution. The coated beads were oven dried after each application. The processing details for the coating are displayed in Table 3, while Table 4 indicates the dissolution profiles for the 50%, 75% and 100% target weight coated beads.

TABLE 2

MORPHINE SULPHATE APPLIED BEADS PROCESSING DETAILS

| MATERIALS | Quantity (Kg) |
|---|---|
| Morphine sulphate | 1.000 |
| Fumaric acid | 1.000 |
| Talc | 0.020 |
| Sodium lauryl sulphate | 0.005 |
| Blend weight | 2.025 |
| Non pareil seeds (0.5–0.6 mm) | 0.500 |
| 17.9% PVP solution | 2.000 |

TABLE 2-continued

MORPHINE SULPHATE APPLIED BEADS PROCESSING DETAILS

| MATERIALS | Quantity (Kg) |
|---|---|
| APPLICATION | |
| Process duration | 140 min |
| Solution spray rate | 5–60 ml/min |
| Powder flow rate | 0–15 rpm |
| Rotor speed | 140 rpm |
| Slit air | 0–2 NM$^3$/min |
| Spray air | 0–1 L/min |
| DRYING | |
| Temperature (° C.) | 50 |
| Duration (h.) | 20.5 |
| DISSOLUTION (%/h.) | 100% released after 0.5. h. |

TABLE 3

MORPHINE SULPHATE SR BEADS PROCESSING DETAILS

| MATERIALS | Quantity (Kg) | | |
|---|---|---|---|
| Applied beads | 0.500 | | |
| Eudragit RL 12.5 | 0.010 | | |
| Eudragit RS 12.5 | 0.190 | | |
| Isopropanol | 0.200 | | |
| Talc | 0.150 | | |
| COATING SOLUTION | 95:5 Eudragit RS 12.5: Eudragit RL 12.5; 6.25% w/w in isopropanol | | |
| Solution flow rate g/TC | 6 | | |
| Talc g/TC | 4 | | |
| Cumulative coating stage | 50% | 75% | 100% |
| Polymer applied mg/g/IR | 18.8 mg/g | 28.1 mg/g | 37.5 mg/g |
| Wt. of coating soln. (Kg) | 0.200 | 0.125 | 0.125 |
| Wt. of talc (Kg) | 0.150 | 0.100 | 0.100 |
| DRYING | | | |
| Temp ° C. | 50 | 50 | 50 |
| Duration (hours) | 22 | | 20.67 |

Encapsulation

The appropriate quantities of both the 100% polymer coat target weight sustained release beads and the applied beads were used to hand-fill hard gelatin capsules to achieve a unit-dose of 60 mg per capsule in a ratio of 9:1. The following dissolution pattern was obtained:

| Dissolution (h.) (water) | % Released |
|---|---|
| 1 | 15.4 |
| 3 | 31.9 |
| 6 | 59.1 |
| 12 | 93.9 |
| 24 | 100.4 |

TABLE 4

MORPHINE SULPHATE SR BEADS DISSOLUTION PROFILES

| STAGE (target weight) | 50% | 75% | 100% | 100% |
|---|---|---|---|---|
| POTENCY (mg/g) | 278.90 | 269.48 | 257.49 | 257.49 |
| DISSOLUTION (%/h.) | | | | |
| 0.5 | 32.5 | 6.9 | −1.2 | — |
| 1 | 65.0 | 17.7 | 2.2 | 3.6 |
| 2 | 92.5 | 40.4 | 8.7 | — |
| 3 | 94.5 | 62.1 | 19.2 | 19.8 |
| 4 | | 76.9 | 30.1 | — |
| 5 | | 86.1 | 39.9 | — |
| 6 | | 89.9 | 50.6 | 50.7 |
| 7 | — | 92.8 | 61.3 | — |
| 8 | — | 93.2 | 69.0 | — |
| 9 | — | | 74.6 | — |
| 10 | — | | 79.5 | — |
| 11 | — | | 82.7 | — |
| 12 | — | | 88.1 | 90.8 |
| 15 | — | | 89.6 | — |
| 18 | — | | 89.6 | — |
| 21 | — | | 91.0 | — |
| 24 | — | | | 101.4 |
| 30 | — | — | — | 102.2 |
| 36 | — | — | — | 103.1 |

To investigate the effect of food on the bioavailability of the formulations of this invention, a 60 mg morphine sulphate formulation similar to the encapsulated 100% polymer coat target weight SR beads/applied beads formulation described above was administered as a single dose under both fed and fasted conditions to 12 male subjects (18 to 37 years) with body weights between 60.0 and 94 kg. There was a seven-day washout period between treatments. For each treatment period, the subjects were fasted overnight for a period of at least 10 hours prior to dosing and, in the case of fasted conditions, for four hours after drug administration. Subjects receiving the medication under fed conditions received a standard high fat breakfast thirty minutes prior to dosing and breakfast was completed within five minutes of dosing. A 7 ml venous blood specimen was obtained at the following times: 0 (predose), 0.5, 1, 1.5, 2, 3, 4, 6, 8, 10, 12, 14, 16, 18, 20, 24, 30 and 36 hours following dosing. Plasma concentrations of morphine and its metabolites (3-glucuronide and 6-glucuronide) were measured by liquid chromatography. There was no obvious food effect observed and the ratio of the fed/fasted treatments were 0.95 for AUC(0–36), 0.90 for AUC(inf), and 1.04 for Cmax for the parent compound.

EXAMPLE 5

Morphine Sulphate 60 mg Capsules

Morphine sulphate capsules were manufactured as follows:

Applied Beads (IR beads)

Following the procedure of Example 4, applied beads were manufactured from the following ingredients:

| INGREDIENT | Relative weights |
|---|---|
| Morphine sulphate | 464 |
| Fumaric acid | 232 |
| Talc | 2 |
| Sodium lauryl sulphate | 9 |
| non pareil seeds (0.5–0.6 mm) | 232 |
| Povidone (Kollidon 30) | 60 |

Sustained Release Beads (SR beads)

Two batches of sustained release beads were manufactured using the applied beads above and the procedures of Example 4. Both batches employed a polymer coating solution containing Eudragit RS: Eudragit RL in a 90:10 ratio. Batch 1 was coated to a level of 42 mg/g of applied beads whereas Batch 2 was coated to a level of 52.5 mg/g of applied beads.

Encapsulation

Appropriate quantities of Batch 1 and Batch 2 beads were used to fill hard gelatin capsules to achieve a unit-dose of 60 mg per capsule. The following in vitro dissolution profiles for Batch 1 and Batch 2 formulations were obtained:

| Dissolution (water) (hr) | Batch 1 % release | Batch 2 % r release |
|---|---|---|
| 1 | 9.3 | 3.5 |
| 3 | 29.9 | 17.6 |
| 6 | 56.5 | 42.3 |
| 12 | 82.9 | 74.7 |
| 24 | 95.4 | 99.1 |

Alternatively, each of these SR bead populations may be blended with applied beads and/or at least one other population of SR beads having a different in vitro dissolution profile and filled into gelatin capsules to provide a dosage form having from 10 mg to 200 mg active.

EXAMPLE 6

Morphine Sulphate 60 mg Capsules

Three different types of morphine sulphate capsules (60 mg) are prepared as follows:

Formulation A

Formulation A contains sustained release beads only at a 60 mg capsule unit dose strength. All other strengths may be calculated by adjusting the values quoted proportionally. Formula range mg/g are also detailed.

| INGREDIENTS | UNIT FORMULA (60 mg capsules) | FORMULA RANGE mg/g |
|---|---|---|
| Morphine sulphate | 60 | 281–346 |
| Sugar spheres (non pareil seeds) | 30 | 141–173 |
| Fumaric acid | 60 | 281–346 |
| Talc | 14–41 | 80–193 |
| Sodium lauryl sulphate | 0.3 | 1.4–1.7 |
| Povidone (Kollidon 30) | 7–15 | 36–85 |
| Ammonio methacrylate Copolymer type A (Eudragit RL) | 0.1–0.3 | 0.6–1.5 |
| Ammonio methacrylate Copolymer type B (Eudragit RS) | 1.9–5.9 | 10.9–27.9 |
| Isopropyl alcohol* | — | — |
| Acetone* | — | — |

*Appears in trace amounts only used for processing.

Formulation B

Formulation B (60 mg capsule unit dose strength) contains a blend of 90% sustained release beads and 10% immediate release beads by potency. All other strengths are in proportion to the values quoted.

| INGREDIENTS | UNIT FORMULA (60 mg capsules) | FORMULA RANGE mg/g |
|---|---|---|
| Morphine sulphate | 60 | 288–349 |
| Sugar spheres (non pareil seeds) | 30 | 144–175 |
| Fumaric acid | 60 | 288–349 |
| Talc | 13–37 | 73–179 |
| Sodium lauryl sulphate | 0.3 | 1.4–1.7 |
| Povidone (Kollidon 30) | 7–15 | 36–86 |
| Ammonio methacrylate Copolymer type A (Eudragit RL) | 0.1–0.3 | 0.5–1.4 |
| Ammonio methacrylate Copolymer type B (Eudragit RS) | 1.7–5.4 | 9.8–25.8 |
| Isopropyl alcohol* | — | — |
| Acetone* | — | — |

*Appears in trace amounts only used for processing.

Formulation C

Formulation C (60 mg capsule unit dose strength) comprises 90% of the active agent as sustained release beads with 10% of the active as an immediate release portion coated onto the sustained release beads.

| INGREDIENTS | UNIT FORMULA (60 mg capsules) | FORMULA RANGE mg/g |
|---|---|---|
| Morphine sulphate | 60 | 292–355 |
| Sugar spheres (non pareil seeds) | 27 | 131–160 |
| Fumaric acid | 60 | 292–355 |
| Talc | 13–37 | 74–182 |
| Sodium lauryl sulphate | 0.3 | 1.5–1.8 |
| Povidone (Kollidon 30) | 7–15 | 37–87 |
| Ammonio methacrylate Copolymer type A (Eudragit RL) | 0.1–0.3 | 0.5–1.4 |
| Ammonio methacrylate Copolymer type B (Eudragit RS) | 1.7–5.4 | 10–26.1 |
| Isopropyl alcohol* | — | — |
| Acetone* | — | — |

*Appears in trace amounts only used for processing.

Applied Beads (IR beads)

A blend of morphine sulphate (49.383% w/w), fumaric acid (49.383% w/w), talc (0.988% w/w) and sodium lauryl sulphate (0.25% w/w) which may or may not be milled through a hammer action mill is applied onto sugar spheres (0.5–0.6 mm) using a povidone solution (w/w in isopropyl alcohol) as a binder. This process is undertaken using a fluidised coating machine. The resultant IR beads are oven dried for 10–20 h. at 40–50° C./30–60% relative humidity (RH) to remove residual solvent (isopropyl alcohol) and to obtain a moisture content of about 3–6%.

Dried beads can be screened using 0.7 mm and 1.5 mm screens with the portion between 0.7 mm and 1.5 mm retained for further processing.

The applied beads comprise:

| Active blend | (as above) | 75.39% |
|---|---|---|
| Povidone solution* | (Solids) | 6% |
| Non pareil seeds | (0.5–0.6 mm) | 18.6% |

*A range of 4.5% to 9.6% is allowed for Povidone usage.

Sustained Release Beads (SR beads)

A polymeric solution consisting of Eudragit RS/Eudiagit RL, preferably in a w/w ratio of 95:5, and an appropriate solvent, such as isopropyl alcohol/acetone, such as a 6.25% w/w solution, is sprayed onto a fluidised bed of IR beads. Talc is added simultaneously to prevent agglomeration, thus enhancing the coating process. Materials are coated to the applied IR beads as follows:

Coating solution: 3 g/min/kg of IR beads

Talc: 1.2 g/min/kg of IR beads

Polymer coating followed by drying at 40–50° C./30–60% RH for 10–20 h. is performed until the target dissolution rate is achieved.

Polymer application in the range 12.5 mg/g IR beads to 37.5 mg/g is allowed to achieve the target rate of dissolution. The formulation complies with that described for Formulation A SR beads.

Encapsulation

Formulation A: A blend of SR beads or one population of SR beads only are encapsulated to achieve a target content weight. The composition of the capsule is as described for Formulation A-SR beads only.

Formulation B: A blend of SR beads and IR beads such as a 8:2 to 20:1 SR:IR bead ratio, especially in a 9:1 ratio by activity (potency) is encapsulated to achieve a target content weight. The composition of the capsule is as described for Formulation B.

Formulation C: The SR beads can further be coated with an IR portion such as coating 10% of the active as an IR portion onto the sustained release beads. This coating step, if employed, is undertaken by applying the requisite quantity of morphine sulphate application blend (as given for applied beads) as a solution or suspension using either purified water and/or isopropyl alcohol and/or acetone. This coating process may be followed by oven drying at 40–50° C./30–60% RH for 10 to 20 h. The composition for the resultant capsules is as detailed for Formulation C.

Dissolution Specifications

The products prepared using any one of the options described above will comply with the in vitro dissolution specification as follows:

| Time (h.) | Specification range % released |
|---|---|
| 1 | *NMT 25 |
| 2 | NMT 25 |
| 3 | NMT 25 |
| 4 | 5–30 |
| 6 | 15–40 |
| 9 | 25–60 |
| 12 | 35–70 |
| 24 | **NLT 70 |

*NMT = not more than
**NLT = not less than

EXAMPLE 7

Single Dose Study Carried Out in Healthy Volunteers to Compare the Relative Bioavailabilty of the Products of Examples 1, 2 and 3 with a Reference Product The study was designed to investigate the pharmacokinetic properties of the four morphine formulations and to investigate the possibility of morphine absorption from these formulations in the lower part of the G.I. tract. The results showed that the rank order of release demonstrated in vitro was also reflected in vivo. The products of Example 1 and 2 showed a sustained release of morphine over 36 hours thus confirming the absorption of morphine from the lower G.I. tract. The relative availability of morphine from the slower products was >100% compared to the reference.

The reference product used in this study was similar to the encapsulated 100% polymer coat target weight SR beads/applied beads formulation of Example 4. The mean dissolution data for the reference product is set out in Table 5 and is graphically represented in FIG. 1.

TABLE 5

MEAN DISSOLUTION RATES

| Time (h) | Reference |
|---|---|
| 1 | 14.4 |
| 2 | 22.4 |
| 3 | 29.6 |
| 4 | 38.2 |
| 6 | 54 |
| 9 | 73.7 |
| 12 | 87.9 |
| 24 | — |

Thus, a comparison of Table 5 with Table 1 shows that the reference product had a faster dissolution rate than any of the products of Example 1, 2 and 3.

This study investigated whether products with a slow release rate in vitro also show an extended release in vivo with absorption occurring further down the G.I. tract. The study was designed to investigate the in vivo release profiles of the products of Examples 1, 2 and 3, which, as shown in Table 1, have a slower in vitro dissolution profile compared to the reference.

The study was designed as an open label, single dose, five treatment, five period, balanced randomised crossover study in 15 subjects. Twelve healthy male volunteers completed all five treatment periods and the results given below are the mean of these twelve subjects.

The mean pharmacokinetic parameters for the four products are presented in Table 6. Because plasma levels of morphine from the slow products were sustained over the sampling period (36 hours), the apparent elimination rate constant could not be accurately estimated for a number of subjects. Consequently, the AUC(inf) for the reference and the product of Example 1 is the mean of 9 subjects, whereas in the case of the product of Example 3 the value for AUC(inf) is the mean of 10 subjects. The AUC(inf) for the product of Example 2 was not estimable for the majority of subjects as a defined elimination phase was not apparent. Thus, the mean kel from the product of Example 1 was used to calculate the AUC(inf) for the product of Example 2 as the formulation of this Example is likely to have a comparable if not lower apparent kel than the product of Example 1.

The mean plasma concentration versus time profiles of morphine from all four formulations are presented in FIG. 2.

The rank order observed in vitro is also demonstrated in the in vivo plasma profiles and the in vivo release profiles. The products of Examples 1 and 2 demonstrated a sustained release of morphine over 36 hours. Although the product of Example 3 has an initial release profile similar to the reference, the levels of morphine were more sustained after 16 hours compared to the reference.

TABLE 6

MEAN PHARMACOKINETIC PARAMETERS

| Parameter | Reference | Example 3 (fast) | Example 1 (medium) | Example 2 (slow) |
|---|---|---|---|---|
| Cmax (ng/ml) | 7.21 + 1.78 | 6.32 + 1.26 | 4.83 + 1.44 | 4.93 + 1.44 |
| AUC (inf) ng/ml/h | 172.12 ± 23.17 | 201.84 ± 62.33 | 211.12 ± 82.13 | 263.42 ± 57.64 |
| AUC (0–36) | 128.02 ± 25.49 | 125.92 ± 25.39 | 109.17 ± 24.00 | 104.55 ± 14.56 |
| Tmax (h) | 5.58 ± 3.31 | 7.96 ± 6.18 | 11.29 ± 8.84 | 14.38 ± 11.02 |
| C24 (ng/ml) | 2.40 ± 0.69 | 3.20 ± 1.46 | 3.16 ± 0.89 | 2.80 ± 0.91 |
| F (rel to ref.) | — | 1.16 ± 0.29 | 1.11 ± 0.40 | 1.57 ± 0.29 |

In vitro dissolution profiles indicated a sufficient distinction between all four products. In contrast, there was very little difference between the reference and the product of Example 3 (fast) and also between the products of Examples 2 (medium) and 1 (slow) in vivo.

The relative bioavailabilities compared to the reference were 116%, 111%, and 157% for the fast (Example 3) medium (Example 1) and slow (Example 2) products respectively. This indicated that the slower products with an extended plasma profile had a higher bioavailability.

The total systemic exposure of morphine as measured by the AUC was highest for the slow product, this confirmed that there was continued absorption of morphine from the slow product (Example 2) in the lower G.I. tract.

The data confirmed the possibility that morphine absorption occurs further down the G.I. tract, probably in the colon.

EXAMPLE 8

Determination of the Mean T50 and the Mean T75 Following Single Dose Administration for the Products of Examples 1–3

Mean T50 and mean T75 data were generated from mean plasma concentration versus time profiles (FIG. 2) of morphine following single dose administration of the products of Examples 1–3. The results are given in Table 7 which shows that these products release morphine in vivo following single dose administration such that the duration over which the plasma level of morphine is equal to or greater than 50% or 75% of the peak plasma concentration is greater than 20 hours or 6 hours, respectively. Example 1 and 2 products exceptionally show T50s greater than 30 hours and T75s of 24 hours.

TABLE 7

SINGLE DOSE ADMINISTRATION

| Parameter | Example 3 | Example 1 | Example 2 |
|---|---|---|---|
| T50 | 22.6 | 35.7 | 35.05 |
| T75 | 7.5 | 24.0 | 24.0 |

EXAMPLE 9

A Study in Healthy Volunteers to Compare the Relative Bioavailability at Steady State of the Once-Daily Morphine Sulphate Formulations of Examples 1 and 2 and a Reference 10 mg Oral Solution Dosed Six Times Daily at Four Hourly Intervals The biostudy of Example 7 compared the in vivo profiles of four morphine sulphate formulations with different in vitro dissolution profiles, following single dose administration. The results from that study showed sustained levels of morphine over 36 hours especially for products with the medium (Example 1) and slow (Example 2) dissolution profiles, confirming morphine absorption in the lower G.I. tract. The aim of this study was to investigate the steady state pharmacokinetics of these two (medium and slow products) 60 mg morphine sulphate formulations and to compare these with a reference IR solution (10 mg dosed 6 times a day), namely a morphine solution sold by Boehringer Ingelheim under the Trade Mark ORAMORPH.

Twelve subjects participated in this three treatment, three period, randomised cross-over study. Subject 7 dropped out after completing treatment periods 1 and 2.

Treatments:

A: 60 mg morphine sulphate capsule as prepared in Example 1 once-daily×5days

B: 60 mg morphine sulphate capsule as prepared in Example 2 once-daily×5days

C: 10 mg reference oral solution dosed 6 times daily× 5days

The results showed that each of the formulations of Examples of 1 and 2 was bioequivalent to the reference (Q4h×6) at steady state in terms of the extent of morphine availability, as measured by AUCss. The Cmaxss of both test formulations tended to be lower than the reference as would be expected for a sustained release formulation.

The mean plasma concentration versus time data is presented in FIG. 3. These data are also tabulated in Table 8. The log 10-transformed data including the 90% confidence intervals for Cmaxss and AUCss comparing the formulations of Examples 1 and 2 with the reference (Q4h×6) are presented in Table 9.

The mean profiles of morphine from each of the formulations of Examples 1 and 2 demonstrated a sustained release of morphine at steady state, with a mean Cmax lower than that obtained for the reference. The formulation of Example 1 had a significantly lower Tmin compared to the reference while the formulation of Example 2 showed a Cmin significantly higher than the reference.

TABLE 8

MEAN MORPHINE NON-TRANSFORMED STEADY STATE PHARMACOKINETIC PARAMETERS (Mean ± SD, 12 subjects)

| Parameter | Treatment A Example 1 | Treatment B Example 2 | Treatment C[a] reference |
|---|---|---|---|
| Cmaxss | 18.18 ± 7.00 | 17.22 ± 6.37 | 19.66 ± 4.49 |
| tmax | 7.83 ± 4.53 | 6.83 ± 4.60 | 8.09 ± 8.07 |
| AUCss | 268.28 ± 79.35 | 276.07 ± 58.40 | 278.80 ± 62.34 |
| Tmin | 16.00 ± 10.23* | 10.00 ± 11.25 | 8.00 ± 6.93 |

TABLE 8-continued

MEAN MORPHINE NON-TRANSFORMED STEADY STATE
PHARMACOKINETIC PARAMETERS (Mean ± SD, 12 subjects)

| Parameter | Treatment A Example 1 | Treatment B Example 2 | Treatment C[a] reference |
|---|---|---|---|
| Thalf | 22.02 ± 46.40 | 18.23 ± 29.59 | 10.22 ± 6.74 |
| kel | 0.02 ± 0.02 | 0.02 ± 0.03 | 0.09 ± 0.04 |
| Cmin | 6.86 ± 2.37 | 7.82 ± 2.64** | 6.61 ± 2.15 |
| Cav | 11.18 ± 3.31 | 11.50 ± 2.43 | 11.62 ± 2.60 |
| Cmax/C24 | 2.87 ± 2.85 | 2.31 ± 1.99 | 2.25 ± 0.82 |
| Cmax-Cmin | 11.32 ± 7.09 | 9.40 ± 6.99 | 13.04 ± 3.85 |
| Cmax/Cmin | 3.12 ± 2.75 | 2.57 ± 2.04 | 3.14 ± 0.84 |
| Cmax-Cmin/Cmin | 2.12 ± 2.75 | 1.57 ± 2.04 | 2.14 ± 0.84 |
| Cmax-Cmin/Cav | 1.05 ± 0.75 | 0.86 ± 0.73 | 1.14 ± 0.29 |
| Fss | 0.98 ± 0.18 | 1.01 ± 0.21 | — |

*p ≦ 0.05 comparing treatment A vs reference
**p <≦ 0.05 comparing treatment B vs reference
a = Eleven subjects completed treatment C

TABLE 9

MEAN MORPHINE LOG10-TRANSFORMED STEADY STATE
PRARMACOKINETIC PARAMETERS (Mean (gsd), 12 subjects)

| Parameter | Treatment A Example 1 | Treatment B Bxampie 2 | Treatment C[a] reference | 90% Confidence intervals |
|---|---|---|---|---|
| Cmaxss | 17.13 (1.42) | 16.40 (1.36) | 19.20 (1.25) | 74–109† 71–104‡ |
| AUCss | 259.00 (1.31) | 270.75 (1.23) | 272.34 (1.26) | 86–107† 90–112† |

† Compare A/C
‡ Compare B/C
[a]Eleven subjects completed treatment C

Following log 10-transformation of the AUCss and Cmaxss data, each of the formulations of Examples 1 and 2 was shown to be bioequivalent to the reference in terms of AUCss comparisons (see Table 9 for 90% confidence intervals).

Overall, the results showed that each of the formulations of Examples 1 and 2 had a sustained release profile of morphine over 24 hours and was bioequivalent to the reference in terms of AUCss.

EXAMPLE 10

Determination of the Mean T50 and the Mean T75 Following Steady State Administration for the Products of Examples 1 and 2

Mean T50 and mean T75 data were generated from mean plasma concentration versus time profiles (FIG. 3) of morphine following steady state administration of the products of Examples 1 and 2. The results are given in Table 10 which shows that these products release morphine in vivo following steady state administration such that the plasma level of morphine is equal to or greater than 50% of the peak plasma concentration over the entire 24 hour dosing period. Further, the Example 1 and 2 products show T75s greater than or equal to 12 hours. The results are shown in Table 10.

TABLE 10

STEADY STATE ADMINISTRATION

| Parameter | Example 1 | Example 2 |
|---|---|---|
| T50 | 24 | 24 |
| T75 | 17 | 15 |

EXAMPLE 11

A Comparison of the Formulations of Examples 1 and 2 with Two Commercially Available Once-Daily Morphine Formulations The formulations of Examples 1 and 2 were compared with two other once daily products currently available in Germany (MST Continus Long (Trade Mark)) and elsewhere (Kapanol (Trade Mark)) following single dose administration.

Treatments
A: Formulation of Example 1, single dose, fasted (12 subjects)
B: Formulation of Example 2, single dose, fasted (12 subjects)
C: Kapanol 20 mg capsule (x3), single dose, fasted (20 subjects) (Faulding) (Reference 1)
D: MST Continus Long 60 mg capsule, single dose, fasted (20 subjects) (Mundi Pharma) (Reference 2)

The mean pharmacokinetic parameters for the reference products 1 and 2 are presented in Table 11.

The mean pharmacokinetic parameters for the products of Examples 1 and 2 are presented in Table 6.

TABLE 11

MEAN PHARMACOKINETIC PARAMETERS (Mean ± SD)

| Parameter | Kapanol 20 mg capsule x 3 | MST Continus Long 60 mg capsule |
|---|---|---|
| Cmax | 8.26 ± 2.72 | 10.72 ± 3.91 |
| Tmax | 8.67 ± 3.57 | 4.06 ± 1.84 |
| AUC (0–36) | 120.04 ± 130.19 | 115.16 ± 30.13 |
| AUC (inf) | 153.61 ± 39.38 | 152.18 ± 47.58 |

FIG. 4 shows the mean plasma profiles of morphine for all four treatments. FIG. 4 demonstrates that the formulations of Examples 1 and 2 had a more rapid onset of delivery than the two reference products. The release from the formulations of Examples 1 and 2 tended to be more sustained and produced much flatter plasma profiles when compared to the reference products. The mean Cmax of the formulations of Examples 1 and 2 was lower than that obtained for the reference products. The bioavailability of the formulations of Examples 1 and 2 was comparable to reference 1 and reference 2. Furthermore, the plasma concentrations of morphine for the formulations of Examples 1 and 2 between 12 and 24 hours were higher than for the reference products.

What is claimed is:

1. An oral morphine multiparticulate formulation for once-daily administration to a patient, comprising sustained release particles each having a core containing water soluble morphine and an osmotic agent, the core being coated with a rate-controlling polymer coat comprised of ammonia methacrylate copolymers in an amount sufficient to achieve therapeutically effective plasma levels of morphine over at least 24 hours in the patient wherein the said osmotic agent is an organic agent.

2. A formulation according to claim 1, wherein a portion or all of the sustained release particles further comprise an immediate release coating applied onto the rate-controlling polymer coat, which immediate release coating comprises water soluble morphine.

3. A formulation according to claim 1, further comprising a portion of immediate release particles each comprising a core of water soluble morphine.

4. A formulation according to claim 1, which comprises at least two populations of sustained release particles having different in vitro dissolution profiles.

5. A formulation according to claim 1, which releases morphine in vivo following single dose administration such that the duration over which the plasma level of morphine is equal to or greater than 50% of the peak plasma concentration is 20 hours or greater.

6. A formulation according to claim 5, wherein the duration is 24 hours or greater.

7. A formulation according to claim 5, wherein the duration is 30 hours or greater.

8. A formulation according to claim 1, which releases morphine in vivo following single dose administration such that the duration over which the plasma level of morphine is equal to or greater than 75% of the peak plasma concentration is 6 hours or greater.

9. A formulation according to claim 8, wherein the duration is 12 hours or greater.

10. A formulation according to claim 8, wherein the duration is 18 hours or greater.

11. A formulation according to claim 1, which releases morphine in vivo at steady state such that the plasma level of morphine over the 24 hour dosing period is equal to or greater than 50% of the peak plasma concentration.

12. A formulation according to claim 1, which releases morphine in vivo at steady state such that the duration over which the plasma level of morphine over the 24 hour dosing period is equal to or greater than 75% of the peak plasma concentration is 12 hours or greater.

13. A formulation according to claim 1, which provides a dissolution profile in aqueous media such that about 3 to 25% of the water soluble morphine is released after 1 hour; about 5 to 35% is released after 4 hours; about 25 to 65% is released after 9 hours; about 35 to 75% is released after 12 hours and at least 70% is released after 24 hours.

14. A formulation according to claim 1, which provides a dissolution profile in aqueous media such that about 10 to 15% of the water soluble morphine is released after 1 hour; about 15 to 30% is released after 4 hours; about 35 to 50% is released after 9 hours; about 45 to 65% is released after 12 hours and at least 80% is released after 24 hours.

15. A formulation according to claim 1, wherein greater than 80% of the formulation is comprised of sustained release particles.

16. A formulation according to claim 1, wherein the rate-controlling polymer coat contains Ammonio Methacrylate Copolymers as described in USP/NF in a ratio of 5:95.

17. A formulation according to claim 1, wherein the organic acid is selected from fumaric acid, adipic acid, ascorbic acid, citric acid, tartaric acid, lactic acid, malic acid or succinic acid.

18. A formulation according to claim 1, wherein the organic acid is fumaric acid.

19. A formulation according to claim 1, wherein the water soluble morphine and osmotic agent are present in the core in a ratio of 1:1.

20. A formulation according to claim 1, wherein the water soluble morphine is morphine sulfate or a hydrate thereof.

21. A formulation according to claim 1, which has a moisture content of about 3–6% by weight.

22. A formulation according to claim 1, wherein the cores for the sustained release particles are equilibrated at ambient conditions or dried at humidified conditions prior to being coated with the rate-controlling polymer coat so as to obtain a moisture content of about 3–6% by weight.

23. A formulation according to claim 1, wherein the sustained release particles following application of the rate-controlling polymer coat are dried at a temperature of about 40–50° C. and about 30–60% relative humidity.

24. A formulation according to claim 1, which contains between 10 mg and 200 mg of morphine sulfate or the equivalent amount of water soluble morphine.

25. A formulation according to claim 1, which is encapsulated.

26. The formulation according to claim 1, wherein the core comprises an inert core upon which a blend comprising the water soluble morphine and an osmotic agent is applied.

27. An oral morphine multiparticulate formulation for once-daily administration to a patient, comprising sustained release particles each having a core containing water soluble morphine and an osmotic agent, the core being coated with a rate-controlling polymer coat comprised of ammonia methacrylate copolymers in an amount sufficient to achieve therapeutically effective plasma levels of morphine over at least 24 hours in the patient, wherein the said osmotic agent is an organic acid, wherein the formulation is characterised by a rapid onset of action and a substantially flat morphine plasma profile.

* * * * *

UNITED STATES PATENT AND TRADEMARK OFFICE
CERTIFICATE OF CORRECTION

PATENT NO. : 6,066,339
DATED : May 23, 2000
INVENTOR(S) : Paul Stark, Sean Cunningham and Jagathesanln Moodley It is certified that error appears in the above-identified patent and that said Letters Patent is hereby corrected as shown below:

<u>Column 20,</u>
Line 67, kindly amend claim 1 as follows:
1     An oral morphine multiparticulate formulation for once-daily administration to a patient, comprising sustained release particles each having a core containing water soluble morphine and an osmotic agent, the core being coated with a rate-controlling polymer coat comprised of ammonia methacrylate copolymers in an amount sufficent to achieve therapeutically effective plasma levels of morphine over at least 24 hours in the patient wherein the said osmotic agent is an organic acid.

Signed and Sealed this

Eighteenth Day of January, 2005

JON W. DUDAS
*Director of the United States Patent and Trademark Office*